United States Patent [19]

Schoenrock et al.

[11] 4,247,636

[45] Jan. 27, 1981

[54] PROCESS FOR PRODUCING A HIGH FRUCTOSE SWEETENER, HIGH PROTEIN MEAL, AND CEREAL GERM OILS

[75] Inventors: Karlheinz W. R. Schoenrock, Ogden, Utah; Thomas H. Henscheid, Twin Falls, Id.; Hugh G. Rounds, Ogden, Utah

[73] Assignee: The Amalgamated Sugar Company, Ogden, Utah

[21] Appl. No.: 955,092

[22] Filed: Oct. 26, 1978

[51] Int. Cl.³ .................................................. C12P 19/24
[52] U.S. Cl. ........................................ 435/94; 435/96; 435/99
[58] Field of Search ............................ 435/94, 96, 99

[56] References Cited

U.S. PATENT DOCUMENTS

| 3,880,742 | 4/1975 | James et al. | 435/200 |
|---|---|---|---|
| 4,025,389 | 5/1977 | Poulsen et al. | 435/94 |
| 4,059,489 | 11/1977 | Meers | 435/94 |
| 4,069,103 | 1/1978 | Muller | 435/99 X |
| 4,081,327 | 3/1978 | Chibata et al. | 435/94 |
| 4,110,163 | 8/1978 | Hjortshoj et al. | 435/200 |

*Primary Examiner*—Lionel M. Shapiro
*Attorney, Agent, or Firm*—Trask & Britt

[57] ABSTRACT

A process for producing highly concentrated syrups by enzyme treatment of impure starch flour containing beta-glucans. High protein meal and cereal germ oils are recoverable as by-products. The impure starch source is ground into flour and slurried with water. Beta-glucanase enzyme is then added and allowed to react. The reacted slurry is treated with alpha-amylase enzyme and is again allowed to react. The solids and cereal germ oils are separated from the aqueous solution and processed into useful by-products. The aqueous solution is then saccharified into a high dextrose solution by the addition of glucoamylase enzyme. The saccharified mixture is filtered, purified and its pH is adjusted to 8.5 with active MgO before isomerization into a high fructose sweetener by conventional means.

21 Claims, 4 Drawing Figures

PROCESS FOR PRODUCING A HIGH FRUCTOSE SWEETENER, HIGH PROTEIN MEAL, AND CEREAL GERM OILS

BACKGROUND OF THE INVENTION

1. Field

The present invention relates generally to the conversion of starches to sweeteners and more particularly to the preparation of high fructose sweeteners from impure barley flour.

2. State of the Art

Starch syrups have been prepared in the past by the hydrolysis of starch suspensions and cereal slurries. Hydrolysis has been effected by heating these solutions and slurries in the presence of dilute acids and by enzyme action. Representative acid amylolysis processes ae shown in U.S. Pat. Nos. 3,200,012 (Hay); 432,358 (Berge); 690,359 (Brown); 2,438,033 (Brown et al); 2,797,176 (Gottfried et al); 2,073,342 (Hart); 246,262 (Williams et al); 2,094,558 (Daly); 1,938,574 (Bauer); 3,383,245 (Scallet et al). In general, these processes involve the breakdown of starch granules, which contain two polymers of (amylose and amylopectin) into glucose units; and the concentration of the glucose into syrups.

Processes utilizing both acid hydrolysis and enzymatic action are described in U.S. Pat. No. 2,137,973 (Daly et al). The combined acid and acid enzyme processes of the prior art described by Daly et al have certain drawbacks, among them being a characteristic bitter taste in the acid-converted syrup when it is concentrated to in excess of about 60 D.E. Various methods are known for minimizing this bitterness. The use of ion exclusion and/or ion exchange columns to eliminate acid by-products is disclosed by U.S. Pat. No. 3,305,395 (Scallett et al) to produce a non-crystallized, very sweet tasting syrup of about 70 to 85 D.E. Crystallization techniques to extract the glucose crystals free from acid by-products in the liquor are discribed in U.S. Pat. Nos. 3,265,533 (Meisel); and 3,236,687 (Smith et al).

An ancient patent disclosing a crude enzymatic process is U.S. Pat. No. 260,853 (Duff). The source of enzymes in that process was "malt". More modern enzyme conversion methods avoid the use of mineral acids in favor of a three enzyme process to convert starch solutions into high fructose sweeteners. These enzymatic catalysis reactions have the advantage of being quite specific so that they avoid the side reactions inherent in the aforedescribed highly acidic hydrolysis methods of producing sweeteners. In the typical sequence of these processes, the starch is first treated with alpha-amylase (alpha-1, 4-Glucan gluconohydrolase) to break down the starch into smaller water soluble fragments in a liquefaction process such as that described by U.S. Pat. No. 3,185,633 (Krebs). These starch fragments are then reacted with glucoamylase (alpha-amyloglucosidase alpha-1, 4-Glucon glucohydrolase) to degrade the fragments into individual glucose molecules. The glucose solution is then treated with glucose isomerase (glucosephosphate isomerase; D-Glucose-6 phosphate ketol isomerase) to convert a portion of the glucose into fructose, and the fructose solution is subsequently purified and concentrated into a colorless syrup. See, for example, U.S. Pat. Nos. 3,285,770 and 3,383,245 (Scallet). Other examples of three enzyme processes for preparing starch syrups from starch solutions are found in U.S. Pat. Nos. 2,891,869 (Langlois); 3,137,639 (Hurst); 3,305,395 (Scallett); and 3,067,066 (Ehrenthal). The historical development and the nature of these three enzyme conversion methods are described by R. V. MacAllister, E. K. Wardrip, and B. J. Schnyder in their article "Modified Starches, Corn Syrups Containing Glucose and Maltose, Corn Syrups Containing Glucose and Fructose, and Crystalline Dextrose", contained in the series of monographs entitled *Enzymes In Food Processing* (Academic Press Inc.; New York, 1975), edited by Gerald Reed. The entire series is descriptive of the technology pertinent to this invention, and is incorporated by reference as a portion of this disclosure.

None of the present three enzyme processes produce a purified and highly concentrated syrup (that is, in excess of about 95 D.E.) directly from the enzyme treatment of slurries of impure starch flour. Most of the present methods for producing such syrup, for example, include a starch recovery step to isolate purified starch prior to enzyme treatment. The use of corn grits as a starting raw material without prior starch separation has been suggested for the preparation of a sweetener. This approach has not yet succeeded commercially because of the inferior quality of the final product, even though the impurities associated with the corn grits are relatively benign when present during the starch hydrolysis procedure. Although the technology for converting purified starch to sweetener is well developed, it has not been successfully applied to the converting of starch sources rich in glucan gums such as are found in barley grains. The presence of these gums interferes with conventional liquification, saccharification and purification procedures. Under the conditions of the aforementioned prior art processes for the production of sweetener from starch, these gums generate high viscosities at low concentrations. This limitation leads to: excessive dilution and high evaporation costs; difficulties in achieving a liquid/solids separation for the removal of insoluble and colloidal impurities; and a low quality final product which is high in color and turbidity, is impure and tends to gelatinize at a concentration of about 70% solids. For the same reasons, it has not been possible to achieve an economical separation of barley starch from barley flour. Accordingly, it has not been practical to produce a purified and concentrated sweetener using barley as the raw material source.

SUMMARY OF THE INVENTION

Applicants' invention eliminates the need for a starch recovery system prior to enzyme treatment of impure starch flours containing beta-glucans. The practice of this invention results in an economical conversion of low cost impure barley starch flours into valuable concentrated sweetener syrups. It also produces a high protein meal and cereal germ oils as by-products.

The present invention comprises a novel process for producing highly concentrated fructose syrups through enzyme treatment of impure starch flour. Typically, the impure starch source is first ground into flour and slurried with water. Usually, roughage, such as grain hulls, is mechanically removed prior to slurrying the flour. Beta-glucanase (preferably bacterial in origin) is desirably next added to the slurry and allowed to react. Alpha-amylase is added to the reacted slurry to liquefy the starch mixture. In practice, commercially available bacterial beta-glucanase contains significant quantities of alpha-amylase and proteinase enzymes. Alpha-amylase is not present in sufficient amount to liquefy the starch, however, when a practical amount of the beta-glucanase is used. The residual solids and cereal germ oils are then separated from the resulting aqueous solution and processed into high protein meal. The glucose solution is then saccharified by treatment with glucoamylase to a D.E. above 90. However, according to certain embodiments of this invention, liquid/solids separation and the purification procedures may be carried out after partial saccharification with soluble glucoamylase, preferably after a D.E. of about 50–70 is reached. In that event, completion of the saccharification step with either soluble or immobilized glucoamylase to a D.E. of above about 90 follows the purification steps. The saccharified mixture is then filtered, purified and concentrated. Its pH is adjusted with active MgO to within the range of 8.0 to 8.5, and it may then be isomerized in conventional fashion by reaction with glucose isomerase to produce a high fructose sweetener.

Steeping of the whole barley in the presence of $SO_2$, e.g. with sulfurous acid ($H_2SO_3$), prior to milling further facilitates purification of the starch hydrolysates and improves the quality of the final product.

The claimed process is particularly well adapted to impure starch sources having high concentrations of beta-glucans. These materials, in combination with the glutens of the grains, have been difficult to separate from the starch in the starch source by conventional techniques. Applicants' use of beta-glucanase enzyme early in the process, the specific sequencing of processing steps disclosed herein, and the use of active MgO for pH adjustment prior to isomerization represent important advances in the state of the art. The steeping procedures of this invention are also novel, and of particular advantage when barley grain is processed.

As used in this disclosure and the appended claims, the following terms should be understood as follows:

"D.E." refers to "dextrose equivalent". Either term is understood within the art to refer to the number of mass units of pure glucose required to reduce the equivalent amount of a standard Fehling's solution reagent as 100 mass units of a dry substance hydrolysate sample.

"Glucans" are amylose and amylopectin compounds found in cereal grains, notably barley. The "gums" present in cereal grains are "beta glucans".

"Gluten" refers to the sticky mixture of proteins found in the seeds of cereal grains which are nearly insoluble in water.

"Cereal grains" include, without limitation, corn, wheat, barley, rye and other grain species eaten by man.

"RDS" refers to "Refractometer Dry Substance". Both terms are understood within the art to define the percent of dry substance in a sample as determined by a standardized optical refractometer technique.

"High fructose sweetener" refers to a sugar solution in which a portion of the glucose has been converted to fructose. A fructose concentration of above about 40 percent by weight, based upon the total weight of the dissolved sugar, is regarded as "high", although concentrations in excess of 55 percent are now commercially produced.

"Impure starch source" refers to grains which may be milled into an "impure flour"; "impure flour" refers to a milled product prior to treatment for the removal of non-saccharide materials.

"Cp" means centipoise.

"Effective amount" means that amount of a substance (e.g., an enzyme) required to achieve a specified purpose to a commercially recognized practical degree having due regard to the influence of temperature, pH and other factors.

"Dextrose solution" refers to a sugar solution with a high (above 90) D.E.

According to a typical procedure of this invention, barley is cleaned and pearled to remove any dirt and hulls present. It is then ground into a medium-fine flour which is slurried with a fluidizing amount of water with adequate mixing to produce a smooth, fluid blend. A ratio of approximately two parts water per part of flour is usually satisfactory. Beta-glucanase enzyme, an enzyme having an affinity for a trimeric part of the beta glucan molecule (in which the beta 1, 3 and beta 1, 4 linkages alternate) and a schism of the nearest adjacent beta 1, 4 linkage, is added along with the water. The temperature and pH of the slurry should be within the ranges appropriate for good activity of the enzyme. A temperature of approximately 50° C. is generally convenient and appropriate. When "Cereflo 200" (an enzyme commercially available from Novo Enzyme Corporation, Wilton, Conn.) is used, about ¼ weight percent, based on the weight of the flour, is normally effective to reduce the viscosity of the slurry to a useful level. The mixture is typically allowed to react at approximately 50° C. for about an hour, and alpha-amylase enzyme, such as that marketed by Novo Enzyme Corporation under the name "Thermamyle 60" is then added. About 1/5 weight percent of this enzyme, based on the starch present, is usually sufficient under conditions in which the reaction mass is heated by direct steam injection to above approximately 90° C. (in some cases, as high as about 105° C.). Desirably, about half of the enzyme is added initially. After approximately 10 minutes, the remaining portion is added, and the reaction is continued at approximately 95° C. for about an additional hour.

The resulting reaction mass may be separated into liquid and solid portions in a decanter centrifuge at approximately 95° C. The insoluble bran, fiber and proteinaceous material removed with the solid phase is then washed and processed in conventional fashion to produce a high protein meal. The wash water is preferably returned for use in slurrying additional flour. Centrifugation or skimming may also be used to recover free cereal germ oil from the liquid phases of the various slurries and reaction masses produced. The aqueous phase should have a D.E. above 15, and its reaction with iodine should be negative. A negative iodine starch reaction is indicative of adequate starch hydrolysis.

After liquid/solid separation, the slurry is cooled to approximately 60° C. The pH of the aqueous phase is adjusted to about 4.5 by addition of a mineral acid, such as sulfuric acid, and glucoamylase is added. The temperature and pH selected may, of course, vary within the ranges suitable for good enzyme activity. An effective amount, usually about 1/5 weight percent based on RDS, of the enzyme (such as that commercially available from Novo Enzyme Corporation under the trade name "AMG 150") is added. The reaction may be maintained at 60° C. with gentle stirring. Under these reaction conditions, a retention time of 40–48 hours is normally required to reach a D.E. above 90. Although the target D.E. is at least 90, it is recognized that on occasion a lower D.E. of "about 90", i.e., above 85, may result. The reaction product may then be filtered, contacted with carbon, and passed through an ion exchange column, all in conventional fashion, to remove the residual impurities. After these purification procedures, the residual solution normally has a D.E. above 95 and is concentrated to about 40 to about 45 RDS. Again, it is recognized that a D.E. below but "about" 95; i.e., above 90, may result in some instances.

Treatment of the whole cereal grain may include a steeping step whereby the whole kernels are treated for an effective period, typically about 20 to about 50 hours at temperatures below about 55° C. in an aqueous solution of about 1/10 to about 1% sulfurous acid. Sufficient liquid is used to immerse the grain. Liquid in excess of this amount is less desirable but operable. Steeping temperatures above 55° C. are undesirable because of the tendency of the mass to gelatinize. Temperatures below 50° C. are effective but less efficient. Ambient temperatures as low as or lower than room temperature are operable. The steeping water preferably percolates countercurrent to the whole kernels, thereby leaching undesirable impurities and toughening the otherwise brittle fiber components of the whole grain. The steeped kernels are milled gently to loosen the hulls, and the milled product is then slurried with water. The hulls are removed by flotation and/or hydrocyclone action. The remaining kernels, which are essentially intact, are milled, slurried in water to establish a ratio of about 35% solids and 65% water and digested with beta-glucanase at about 50° C. for about one hour to achieve a viscosity below about 1000 cp.

Another variation of the treatment delays the liquid solids separation until a D.E. of over 50 is attained, usually after less than 10 hours of treatment with less than half of the normally added amyloglucosidase. The ion exchange treatment normally carried out after completion of the saccharification step of conventional starch conversion processes may also conveniently be carried out after partial saccharification. The elimination of ionized impurities after partial saccharification enhances product quality. The carbon treatment for color elimination in the enzyme treated starch hydrolysate may be delayed until after completion of saccharification or it may be included after partial saccharification and liquid/solids separation but before the ion exchange treatment.

Completion of the saccharification reaction to a D.E. of over 90 for unpurified hydrolysates or over 95 for ion exchange treated starch hydrolysates is continued with additional amyloglucosidase. The enzyme may be introduced in its soluble form, but is preferably used at this stage in its immobilized form. The reaction is preferably conducted by percolating the partially saccharified hydrolysate through a bed of immobilized amyloglucosidase. The pH of the solution is then adjusted to within the range of about 8 to about 8.5. The use of active MgO is highly preferred and is regarded as superior to other means of activating glucose isomerase enzyme. The solution may then be isomerized with glucose isomerase following conventional procedures at approximately 65° C. The isomerized syrup is again purified and is concentrated to a high fructose syrup of approximately 72% dry substance.

BRIEF DESCRIPTION OF THE DRAWINGS

In the drawings, which illustrate that which is presently regarded as the best mode for carrying out the invention.

DESCRIPTION OF THE ILLUSTRATED EMBODIMENTS

Figure 1:
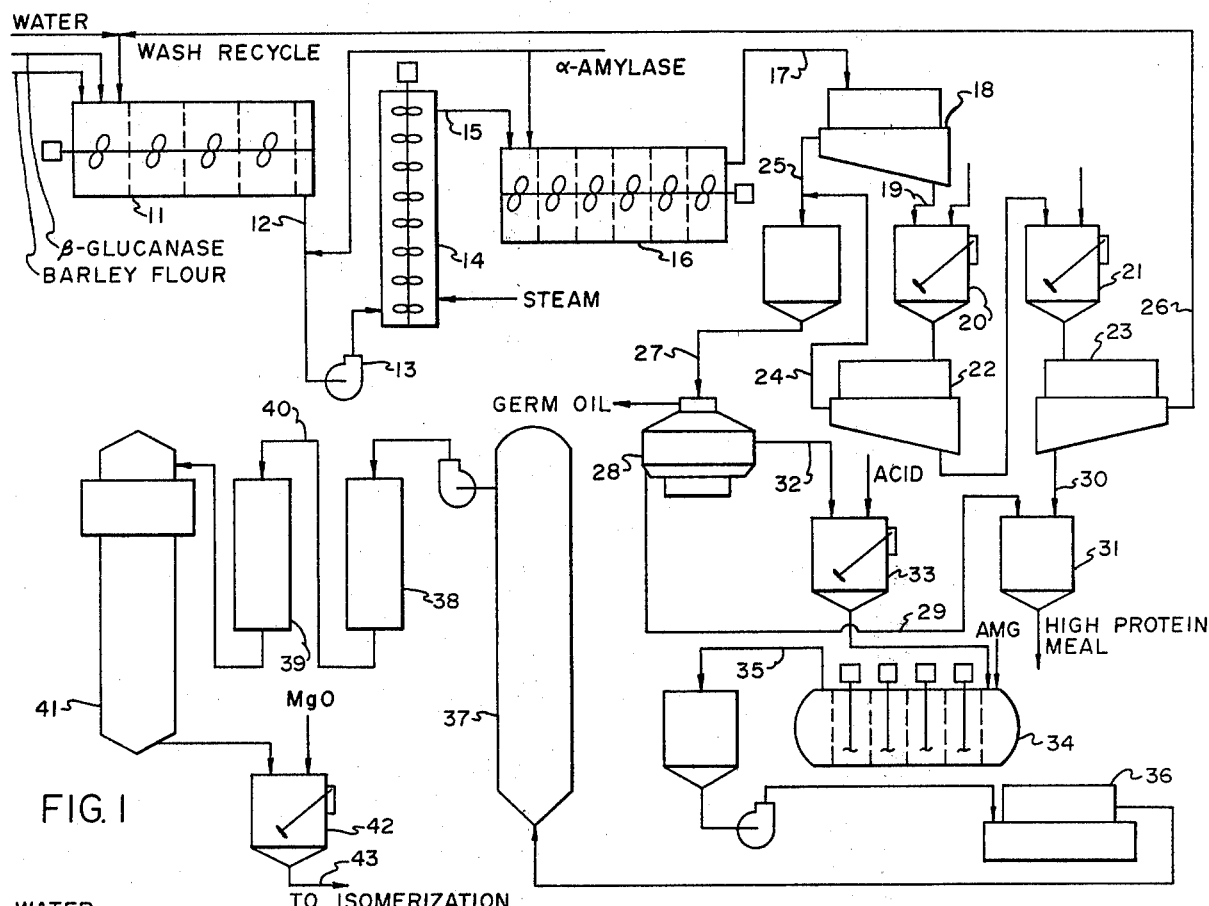
FIG. 1 is a flow diagram of a plant installation embodying the invention.

The following example describes the process as depicted in FIG. 1. It should be understood that the process may be run as either a batch or continuous operation. All quantities specified in the example are scaled to the treatment of 100 pounds of whole kernel barley grain.

EXAMPLE 100 pounds of medium fine barley flour are mixed with about 200 pounds of water in a gum dispersion tank 11. This mixture is mildly heated to about 50° C. while adding 4 ounces of beta-glucanase enzynme (Novo Cereflo Enzyme or equivalent). The mixture is agitated for about 1 hour after which the viscosity of the mixture 12 is reduced to about 500 centipois. Approximately 2½ ozs. of an alpha-amylase enzyme (such as that marketed by Novo Enzyme Corporation under the tradename Thermamyl) is added, e.g., by blending in a pump 13, and the entire mixture is quickly heated to about 95° C. by direct steam injection for about 10 minutes in a first stage liquification reactor 14. The reactor 14 illustrated is specially designed for this operation to provide high shear and agitation under conditions of high plasticity. After about 10 minutes, the reaction mixture 15 has sufficiently thinned to allow additional enzymatically catylized hydrolyses of the starch under more gentle agitation. Additional enzyme is added to the mixture 15 in a second stage liquification reactor 16 wherein the resulting liquified mixture 17 reaches a D.E. of over 15 after about 60 minutes of residence time at about 95° C. A conventional starch reaction of the mixture 17 with iodine should be negative. The liquified mixture 17 is taken through a decanter centrifuge 18 to separate suspended solids 19. The separated solids 19 are reslurried twice with 100 lbs. of water in tanks 20, 21 associated with a first wash decanter centrifuge 22 and a second wash decanter centrifuge 23, respectively. The first wash 24 is combined with the centrifugate 25 of the first centrifuge 18, and the second wash 26 is recycled to the beginning of the process for use in slurrying barley flour. Remaining turbidity in the combined centrifugate 27 is next removed by processing through a solid bowl desludger centrifuge 28 (and/or by filtration through a precoat filter).

Combined solids 29, 30 from the decanter centrifuge 23 and the desludger centrifuge 28, respectively, are processed by drying 31 into a high protein meal suitable for use either as a human food supplement, for example in breakfast cereals, or a high protein animal feed supplement. Its protein content is above 40%, based on total dry solids.

The clarified centrifugate 32 is next cooled to 60° C., adjusted in a mixing tank 33 to pH 4.5 with sulfuric acid, and treated in a saccharification reactor 34 with about 2¼ ozs. of an amyloglucosidase enzyme (such as that marketed by Novo Enzyme Corporation under the trade name "AMG") for about 45 hours under gentle stirring. At the end of this period, the hydrolysate 35 has a D.E. of over 90. The liquid hydrolysate 35 is filtered through a precoat filter 36, and is then decolorized with active granular carbon 37 and an ion exchange treatment, first over the hydrogen form of a strong cation exchanger 38 having sulfonic functional groups, followed by treatment over the hydroxyl form of a weakly basic anion exchanger 39 having predominantly tertiary amine functionality.

A water white, clear dextrose liquor 40 having a D.E. of over 95 is recovered from the ion exchange treatment. This dextrose liquor 40 is concentrated to about 45% dissolved solids in an evaporator 41. Its pH is then adjusted to within the range of about 8 to about 8.5 with active magnesium oxide in a mixing tank 42. Ideally, the ratio of dissolved magnesium to calcium is adjusted to at least 20:1 in the tank 42. The resulting liquor 43 is then ready for treatment with a glucose isomerase (such as that marketed by Novo Enzyme Corporation under the trade name "Sweetzyme") to produce a high fructose sweetener.

Figure 2:
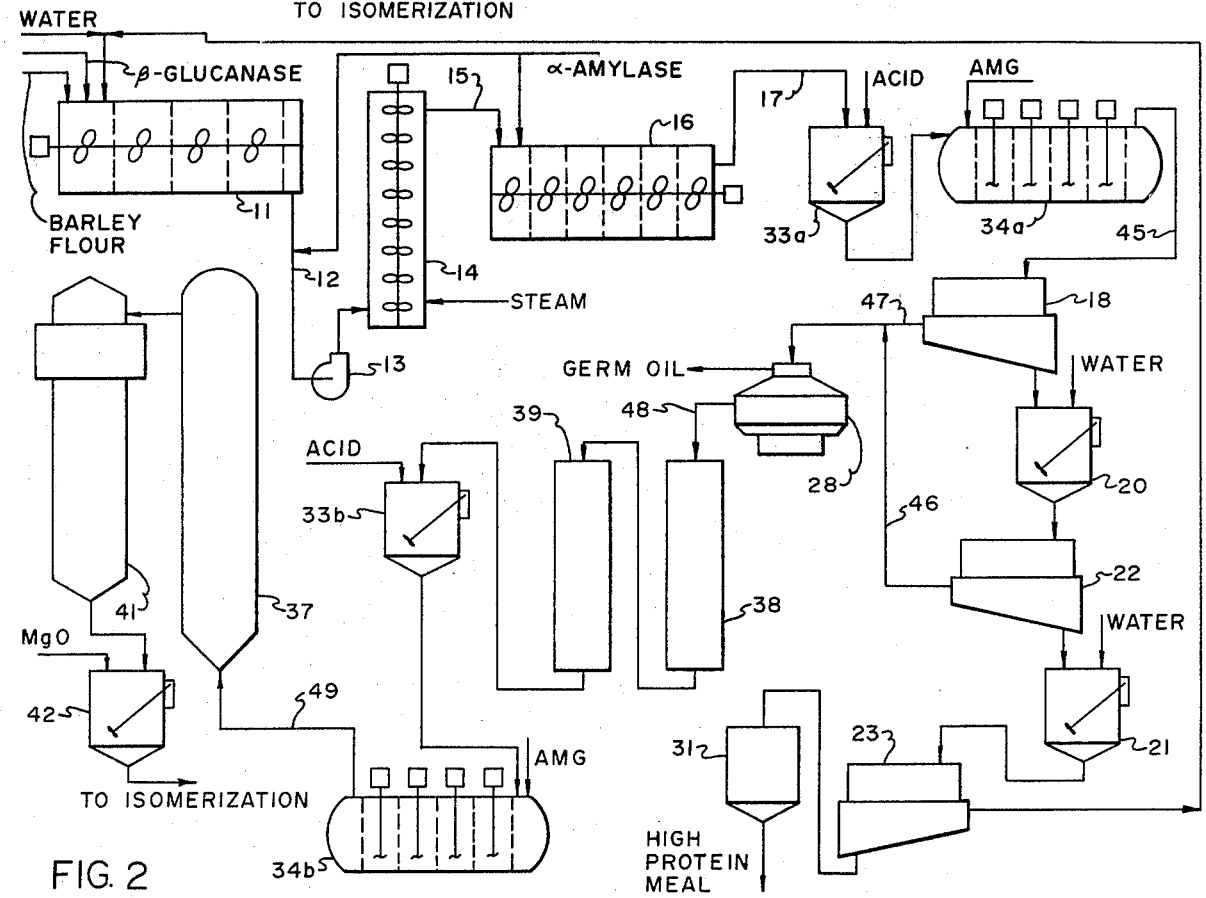
FIG. 2 is a flow diagram of a second plant installation embodying the invention in a modified form.

FIG. 2 illustrates a process similar to that of FIG. 1. Similar equipment and unit operations are designated with identical numerals on the drawings. According to the embodiment illustrated by FIG. 2, the saccharification step is divided into two stages such that no more than approximately half of the glucoamylase enzyme (AMG) is added in a first saccharification reactor 34a and allowed to react for a period of about one to about 10 hours. The partially saccharified liquor 45 is processed through the decanter centrifuges 18, 22, 23 as previously described to recover high protein meal. The first wash 46 is combined with the centrifugate 47 and processed through the desludger centrifuge 28 to recover germ oil. The remaining liquor 48 may then be purified by ion exchange as illustrated (38, 39) or it may be passed directly to a second stage saccharification reactor 34b. During the second stage saccharification, the remaining glucoamylase enzynme is added and allowed to react until the discharge liquor 49 has achieved a D.E. of at least about 90. It is preferred to use an immobilized form of the enzyme for saccharification in the second stage reactor 34b.

Figure 3:
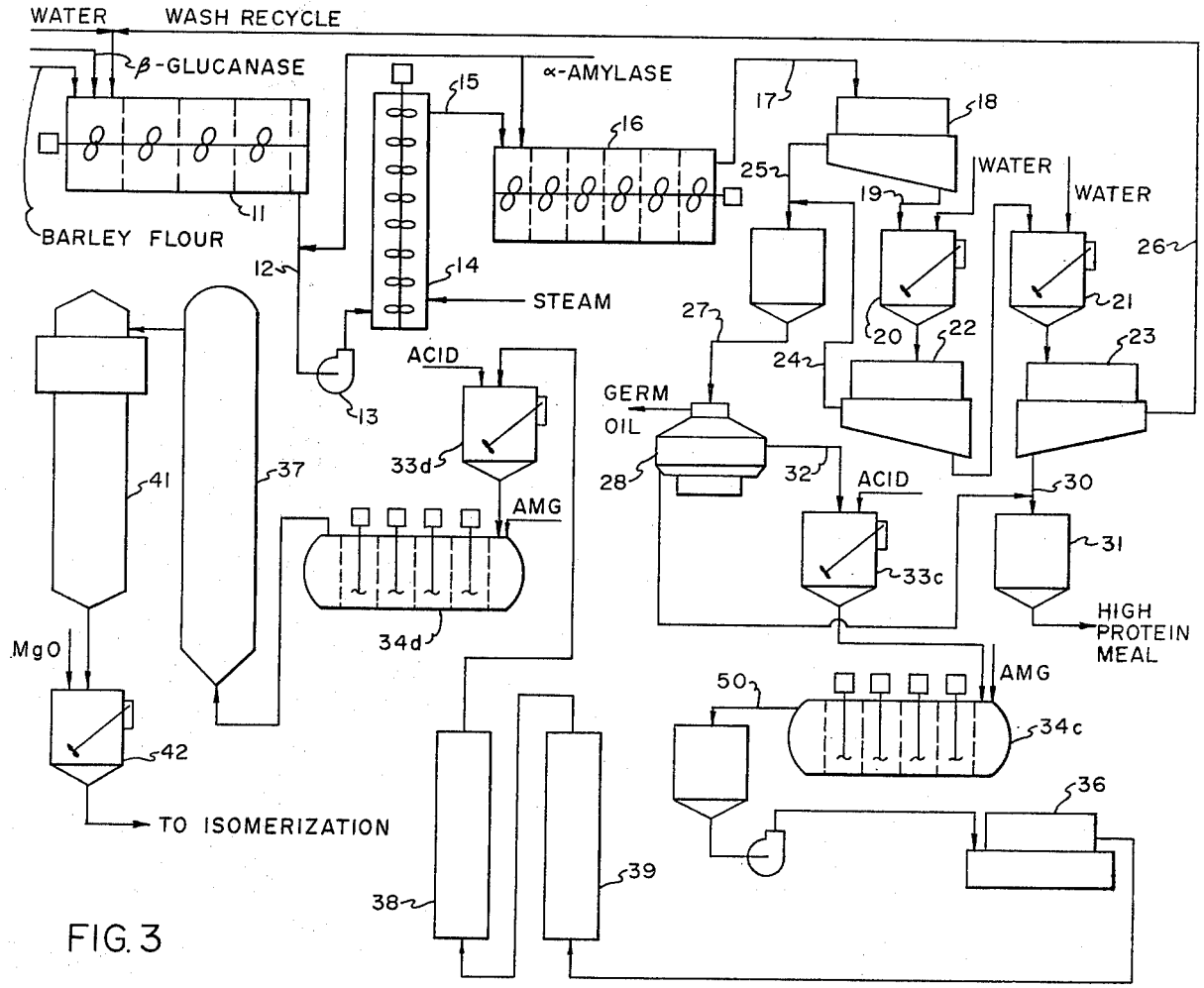
FIG. 3 is a flow diagram of a third plant installation embodying the invention in another modified form.

The process illustrated by FIG. 3 differs from that of FIG. 2 in that partial saccharification (34c) is delayed until after the liquid/solids separation procedures (18-32) are completed. This process nevertheless subjects the discharge liquor 50 from the first stage saccharification reactor 34c to precoat filtration 36 and ion exchange 38, 39 procedures, after which saccharification is completed in a second stage reactor 34d. As previously indicated, FIGS. 2 and 3 are merely illustrative of the various sequence modifications to the process which may be selected in certain circumstances.

Figure 4:
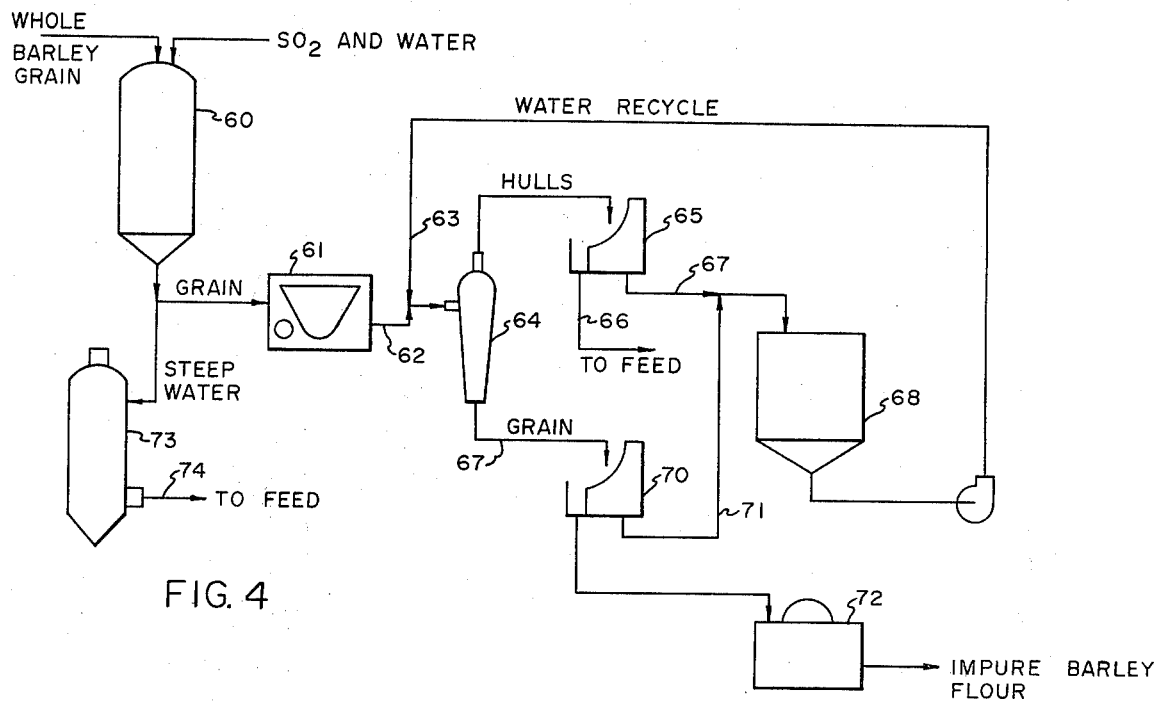
FIG. 4 is a flow diagram of a highly preferred unit operation forming a portion of certain embodiments of the invention.

FIG. 4 illustrates a highly preferred sequence for producing an impure barley flour for processing in accordance with this invention. Whole barley grain is introduced to steep tanks 60. Steeping is preferably conducted in counter current steps at about 40° C. to about 60° C. (preferably below about 55° C.) in the presence of $SO_2$. Steeping softens the barley kernels so that solubles can diffuse into the steep water. Moreover, the $SO_2$ attacks the protein present in the cell walls so that starch is more readily extracted. Increasing the number of steps in the steeping operation increases the RDS of the resulting steep water. A typical steep may be conducted for about 30 to about 50 hours in the presence of an aqueous solution of sodium bisulfite or sulfur dioxide. The use of an aqueous solution of about 1/10 to about 1 percent by weight sulfurous acid as a steeping medium yields consistently satisfactory results. Optimum steep conditions are presently considered to be about 36 to about 48 hours in a steeping solution containing 2/10 to 3/10 percent by weight $SO_2$ at about 50° C. The effective range of $SO_2$ concentration is widely variable, depending in part upon residence time and the character of the barley grain being steeped.

After steeping, the grain is milled 61 to remove the hulls. The milled product 62 is slurried with a stream 63 of water, and the slurry is passed through a separator 64 which separates the grain from the hulls. The separator overflow is taken to a dewatering operation 65. The hulls 66 are recovered for feed, and the water 67 is collected in a tank 68, as shown, for recycling. The grain 69 discharge is also dewatered 70. The recovered water 71 is salvaged for recycle, and the grain is milled 72 to an impure barley flour for further processing in accordance with this invention. The recovered steep water is evaporated 73 to recover the dissolved solids 74.

Applicants' process may be modified by those skilled in the art to operate within the optimum ranges of the reaction parameters of the enzymes specified or their functional equivalents. Those skilled in the art will be guided in such modification by readily available literature, including the aforementioned *Enzymes In Food Science*, edited by Gerald Reed; the references cited herein, and the patent literature cited in this disclosure, all of which are incorporated herein by reference.

Those skilled in the art will recognize that reference herein to details of the illustrated embodiments is not intended to restrict the scope of the appended claims. Reference to optimum temperatures, for example, must be read within the context of the examples given. In the relevant art, the interdependence of parameters, such as pH, temperature, residence time, mixing efficiency and enzyme activity are well understood. Following the teachings of this disclosure, the routineer will be able readily to select operating parameters and quantities which are effective to take full advantage of applicants' invention.

We claim:

1. A process for producing a high fructose sweetener from an impure starch source containing beta glucans comprising:

milling the starch source to produce an impure flour;

mixing the impure flour with sufficient water to produce a fluid mixture;

treating the fluid mixture with an effective amount of beta-glucanase under conditions to produce a slurry of undissolved solid phase in an aqueous phase containing dissolved saccharide materials together with an immiscible organic liquid phase, said slurry achieving a viscosity below about 1000 centipoise within about an hour;

treating the slurry with an effective amount of alpha-amylase under conditions wherein the aqueous phase achieves a D.E. of at least about 15 and the starch reaction with iodine is negative;

treating the aqueous phase of said slurry with an effective amount of glucoamylase under conditions to convert substantially all of the saccharide material in said aqueous phase to glucose, thereby obtaining a glucose enriched aqueous phase;

purifying said aqueous phase to at least 95 D.E.; and subjecting said purified and glucose enriched aqueous phase to enzymatic isomerization, thereby to convert a portion of the glucose therein to fructose.

2. A process according to claim 1 wherein the impure starch source includes barley grain, and said barley grain is first milled to produce pearled barley, and the pearled barley is thereafter milled to produce impure barley flour.

3. A process according to claim 1 wherein whole barley grain is steeped for at least about 20 hours in an aqueous solution containing an effective amount of dissolved $SO_2$ at an effective temperature below about 55° C.

4. A method according to claim 3 wherein whole barley is steeped at a temperature below about 55° C. in an aqueous solution containing about 0.1 to about 1 percent by weight sulfurous acid for between about 30 and about 50 hours; the steeped barley is recovered and gently milled, thereby releasing the hulls and fibers from the kernels of said barley; the hulls and fibers are separated from the kernels by flotation; the kernels are milled and digested in an aqueous suspension in the presence of an effective amount of beta-gluconase enzyme, the starch present in the suspension is liquified with an effective amount of alpha-amylase; the suspended solids are removed, leaving a solution of liquified saccharides; and the liquified saccharides in said solution are saccharified by contacting the solution with an effective amount of gluco-amylase to increase the D.E. of the solution to above 90, thereby producing a dextrose solution.

5. A process according to claim 4 wherein said suspension is passed first through a decanter centrifuge, thereby recovering said suspended solids and is thereafter passed through a desludger centrifuge, thereby recovering said organic liquid phase.

6. A process according to claim 4 wherein said suspended solids are removed by passing said suspension first through a decanter centrifuge and thereafter through a precoat filtration procedure.

7. An improvement according to claim 4 wherein the dextrose solution is purified by filtration, decolorization and demineralization to a D.E. of at least 95; the pH of said purified dextrose solution is adjusted to the range of about 8 to about 8.5 by the addition of magnesium oxide; and the dextrose solution is thereafter contacted with an effective amount of glucose isomerase to produce a high fructose sweetener.

8. A process according to claim 1 wherein the glucose enriched aqueous phase is purified following treatment of the aqueous phase with glucoamylase.

9. A process according to claim 1 wherein the aqueous phase is separated from any solid matter in said slurry following treatment with alpha-amylase enzyme, is recovered, and is thereafter treated with said glucoamylase.

10. A process according to claim 9 wherein the aqueous phase is first recovered from said slurry, is then purified by filtration, decolorization and demineralization procedures and is thereafter treated with said glucoamylase.

11. A process according to claim 1 wherein the aqueous phase is treated with glucoamylase in two stages, whereby:
during the first stage, no more than about half of the enzyme is added and allowed to react for about one to about 10 hours; and
during the second stage, the remainder of the enzyme is added and allowed to react until the aqueous phase has reached a D.E. of at least about 90.

12. A method according to claim 11 wherein the aqueous phase is separated from any solid matter present following the first stage of glucoamylase treatment and prior to the second stage of glucoamylase treatment.

13. A process according to claim 12 wherein the aqueous phase is first recovered and is then purified by filtration, decolorization and demineralization procedures prior to the second stage of glucoamylase treatment.

14. A process according to claim 11 wherein an immobilized form of glucoamylase enzyme is used for said second stage of glucoamylase treatment.

15. A process according to claim 1 wherein said slurry is processed to separately recover said solids and said immiscible organic liquid phase.

16. A process according to claim 15 wherein said slurry is passed first through a decanter centrifuge, thereby recovering said solids and is thereafter passed through a desludger centrifuge, thereby recovering said organic liquid phase.

17. In the process for producing a high fructose sweetener from an impure flour produced by milling barley grain by the enzymatic hydrolysis of the starch content of said flour, the improvement which comprises:
slurrying said impure flour with a fluidizing amount of water in the presence of an effective amount of beta-glucanase enzyme under temperature and pH conditions compatible with said enzyme until the viscosity of the resulting slurry is below about 1000 centipoise.

18. The improvement of claim 17 wherein said beta-glucanase enzyme is associated with alpha-amylase enzyme.

19. The improvement of claim 17 wherein said beta-glucanase is bacterial in origin.

20. In the process for converting a purified dextrose liquor into a high fructose sweetener by reacting said liquor with glucose isomerase enzyme, the improvement which comprises adding active magnesium oxide to said liquor until its pH is adjusted to the range of about 8 to about 8.5 and thereafter treating said liquor with an effective amount of said enzyme to convert at least 40 percent by weight of the glucose therein to fructose.

21. An improvement according to claim 20 wherein the molar ratio of dissolved magnesium to dissolved calcium in said liquor is adjusted to at least 20:1 prior to addition of said enzyme.

* * * * *